US00PP27648P3

(12) United States Plant Patent
Lord

(10) Patent No.: US PP27,648 P3
(45) Date of Patent: Feb. 7, 2017

(54) ***COPROSMA* PLANT NAMED 'COPJOH02'**

(50) Latin Name: *Coprosma repens*
Varietal Denomination: COPJOH02

(71) Applicant: John Lord, Woodbridge (GB)

(72) Inventor: John Lord, Woodbridge (GB)

( * ) Notice: Subject to any disclaimer, the term of this patent is extended or adjusted under 35 U.S.C. 154(b) by 65 days.

(21) Appl. No.: 14/545,460

(22) Filed: May 5, 2015

(65) Prior Publication Data

US 2016/0330888 P1 Nov. 10, 2016

(51) Int. Cl.
*A01H 5/12* (2006.01)

(52) U.S. Cl.
USPC ..... Plt./226

(58) Field of Classification Search
USPC ..... Plt./226
See application file for complete search history.

*Primary Examiner* — Anne Grunberg
(74) *Attorney, Agent, or Firm* — Cassandra Bright

(57) ABSTRACT

A new and distinct *Coprosma repens* named 'COPJOH02' is disclosed, characterized by vibrant burgundy foliage with a bright pink margin and shiny, narrow leaves. Plant habit is upright and plants are useful for colorful Winter plantings. The new cultivar is a *Coprosma repens*, typically suited for ornamental container and landscape use.

1 Drawing Sheet

Latin name of the genus and species: *Coprosma repens*. Variety denomination: 'COPJOH02'.

BACKGROUND OF THE INVENTION

The new cultivar is the result of chance discovery in a commercial nursery in Suffolk, England. The inventor, John Lord, a citizen of England, discovered the new variety as a single branch, naturally occurring mutation growing in a commercial planting of the parent variety *Coprosma repens* 'JWNCOPPS' U.S. Plant Pat. No. 22,607. The discovery was made in the Summer of 2008.

After selecting and isolating the new cultivar, the inventor continued evaluating and testing the new variety. A final selection of the new cultivar 'COPJOH02' was made in the same commercial nursery in Summer of 2010. First propagation was performed by vegetative cuttings during the Summer of 2008. After the final selection of 'COPJOH02' during 2010, 2 additional generations have been propagated. This subsequent propagation has shown the unique features of this cultivar are stable and reproduced true to type.

SUMMARY OF THE INVENTION

The cultivar 'COPJOH02' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'COPJOH02'. These characteristics in combination distinguish 'COPJOH02' as a new and distinct *Coprosma* cultivar:

1. Vibrant foliage with a burgundy center and bright pink margin.
2. Glossy foliage.
3. Upright plant habit.
4. Usefulness for Winter ornamental interest

PARENTAL COMPARISON

Plants of the new cultivar 'COPJOH02' are similar to the parent, 'JWNCOPPS' in most horticultural characteristics. However, 'COPJOH02' differs in foliage color. Foliage of the new variety is distinctly burgundy in the center, with a bright pink margin. Foliage of the parent variety has a Greyed-Red mid-section and a Greyed-Purple margin.

COMMERCIAL COMPARISON

Plants of the new cultivar 'COPJOH02' can be compared to the patented commercial variety *Coprosma* 'Fireburst' U.S. Plant Pat No. 14,906. Plants of 'COPJOH02' are similar to 'Fireburst' in most horticultural characteristics, however, 'COPJOH02' has more vibrantly colored foliage, with a burgundy center and bright pink margins. Foliage of 'Fireburst' is yellow-green in the center with a medium pink edge.

BRIEF DESCRIPTION OF THE PHOTOGRAPH

The accompanying photograph in FIG. 1 illustrates in full color a typical plant of 'COPJOH02' grown outdoors in Silvan, Victoria, Australia This plant is approximately 18 months old, shown in a 3 liter pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'COPJOH02' plants grown outdoors in Silvan, Victoria, Australia. Temperatures ranged from approximately 7° C. to 10° C. at night to 15° C. to 30° C. during the day. No artificial light, photoperiodic treatments or chemical treatments were given to the plants. Measurements and numerical values represent averages of typical plant types.

Botanical classification: *Coprosma repens* 'COPJOH02'.

Age of the plant described: Approximately 18 months.

Container size of the plant described: 3 liter commercial container.

PROPAGATION

Time to initiate roots: Summer: 20 to 25 days at approximately 20° C.

Root description: Fine, densely branched, non-fibrous, non-fleshy

PLANT

Growth habit: Upright.

Pot size of plant described: 3 liter.

Height: Approximately 50 cm from soil line to top leaf, after 5 years.

Plant spread: Approximately 30 cm after 5 years.

Stem diameter: Approximately 0.3 cm.

Stem color: Near RHS Greyed-Green 197A.

Branching characteristics: Moderately well-branched, bushy and upright habit.

Length of primary lateral branches: Average range from 10 to 25 cm.

FOLIAGE

Leaf:

*Arrangement*.—Opposite, sessile.

*Average leaves per lateral branch*.—Approximately 10 to 20.

*Average length*.—2 to 4 cm.

*Average width*.—1 to 2 cm.

*Shape of blade*.—Oblanceolate.

*Apex*.—Obtuse.

*Base*.—Attenuate.

*Margin*.—Entire.

*Texture of top surface*.—Shiny, leathery.

*Texture of bottom surface*.—Shiny, leathery.

*Pubescence*.—Non pubescent all surfaces.

*Aspect*.—Undulating or rolled margins, slight twist to overall leaf blade.

*Color*.—Young foliage upper side: Center near RHS Purple N77A, margin near Red-Purple N57A. Young foliage under side: Center near RHS Purple N77A, margin near Red-Purple N57A. Mature foliage upper side: Center near RHS Purple N77A, margin near Red-Purple N57A. Mature foliage under side: Center near RHS Purple N77A, margin near Red-Purple N57A.

*Venation*.—Type: Pinnate. Venation color upper side: Indistinguishable from leaf blade. Venation color under side: Indistinguishable from leaf blade.

FLOWER

Flower type: Only male flowers observed to date. Small, polypetalus, flowers occurring in axillary umbels. Corolla described, calyx present, however, too minute to measure.

Male flower description:

*Flowers per umbel:* 10 to 20.

*Flowering season*.—Spring.

*Length of flowering*.—Approximately 2 weeks.

*Flower length*.—Approximately 0.4 cm.

*Flower width*.—Approximately 0.2 cm.

*Outer flower surface color*.—Near RHS Yellow-Green 151C.

*Inner flower surface color*.—Near RHS Yellow-Green 150C.

*Petal length*.—Approximately 0.3 cm.

*Petal width*.—Approximately 0.1 cm.

Stamens:

*Quantity*.—5.

*Filament length*.—0.3 cm.

*Filament color*.—Near RHS Yellow-Green 150C.

*Anther shape*.—Oblong.

*Anther length*.—Approximately 0.1 cm.

*Anther color*.—Near RHS Yellow 7C.

*Pollen color*.—Near RHS Black 202A.

OTHER CHARACTERISTICS

Seeds and fruits: Not observed to date.

Disease/pest resistance: Neither resistance nor susceptibility to normal diseases and pests of *Coprosma* has been observed.

Temperature tolerance: The new variety tolerates low temperatures to approximately −5° C. and has been observed to tolerate high temperatures to at least 30° C.

What is claimed is:

1. A new and distinct cultivar of *Coprosma repens* plant named 'COPJOH02' as herein illustrated and described.

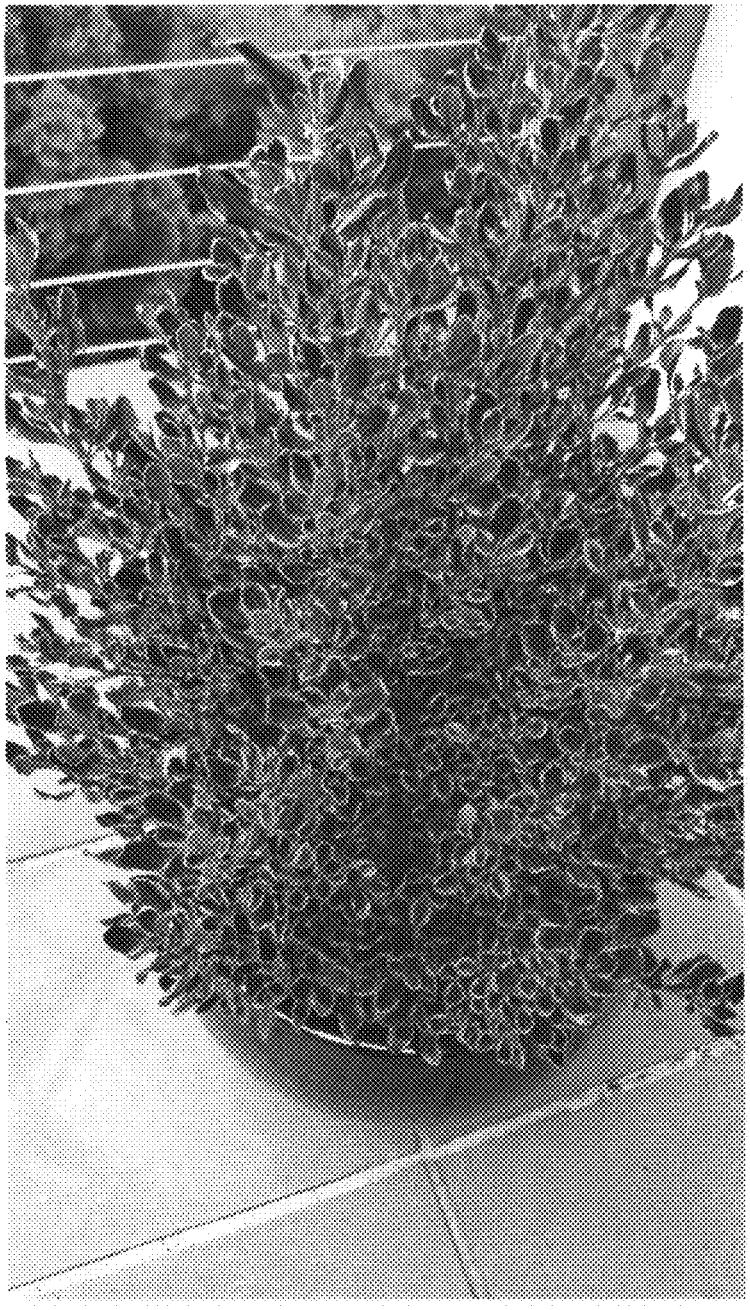

* * * * *